(12) United States Patent
Gerber

(10) Patent No.: US 9,151,462 B2
(45) Date of Patent: Oct. 6, 2015

(54) LIGHT GUIDE DIFFUSER, AND METHODS

(71) Applicant: GR Enterprises and Technologies, Woodbridge, CT (US)

(72) Inventor: Mark J. Gerber, Avon, CT (US)

(73) Assignee: GR Enterprises and Technologies, Woodbridge, CT (US)

( * ) Notice: Subject to any disclaimer, the term of this patent is extended or adjusted under 35 U.S.C. 154(b) by 247 days.

(21) Appl. No.: 13/625,357

(22) Filed: Sep. 24, 2012

(65) Prior Publication Data

US 2013/0163274 A1   Jun. 27, 2013

Related U.S. Application Data

(60) Provisional application No. 61/578,428, filed on Dec. 21, 2011.

(51) Int. Cl.
*A61B 1/06* (2006.01)
*F21V 7/00* (2006.01)
*A61B 19/00* (2006.01)
*F21W 131/205* (2006.01)

(52) U.S. Cl.
CPC ............... *F21V 7/00* (2013.01); *A61B 19/5202* (2013.01); *F21W 2131/205* (2013.01)

(58) Field of Classification Search
CPC ...... G02B 6/0001; G02B 6/0096; G02B 6/10; F21V 2008/003; F21V 2008/008; F21V 7/04; F21W 2131/20
USPC .............. 362/16, 558, 559, 560, 572, 296.01, 362/307, 311.01, 311.06, 347
See application file for complete search history.

(56) References Cited

U.S. PATENT DOCUMENTS

| 2,259,910 A | * | 10/1941 | Rylsky, V | 362/26 |
|---|---|---|---|---|
| 2,360,663 A | * | 10/1944 | Eddy | 250/227.11 |
| 3,474,242 A | * | 10/1969 | Forrant | 362/7 |
| 4,605,990 A | | 8/1986 | Wilder et al. | |
| 5,115,126 A | | 5/1992 | Ams et al. | |
| 5,353,786 A | | 10/1994 | Wilk | |
| 5,488,696 A | | 1/1996 | Brosnan | |
| 5,785,648 A | | 7/1998 | Min | |
| 5,850,496 A | | 12/1998 | Bellahsene et al. | |
| 6,616,603 B1 | | 9/2003 | Fontana | |
| 6,880,945 B2 | * | 4/2005 | Knaack et al. | 362/26 |
| 7,150,714 B2 | | 12/2006 | Myles | |
| 7,407,311 B2 | * | 8/2008 | Yang | 362/555 |
| 7,460,751 B2 | * | 12/2008 | Gomez Ruiz | 385/39 |
| 7,486,885 B2 | * | 2/2009 | Tenmyo | 396/198 |
| 7,712,907 B2 | * | 5/2010 | Zyka | 362/16 |

(Continued)

OTHER PUBLICATIONS

Edmund Optics Inc., 2013, Fiber Optic Ring Light Guides [retrieved on Mar. 18, 2014]. Retrieved from the Internet: <http://www.edmundoptics.com/illumination/fiber-optic-illumination/fiber-optic-light-guides/fiber-optic-ring-light-guides/1432>.

*Primary Examiner* — Ismael Negron
(74) *Attorney, Agent, or Firm* — McCarter & English, LLP

(57) ABSTRACT

Systems, devices and methods for illuminating sites (e.g., surgical sites) are provided. An illumination device (e.g., a surgical site light) includes a body (e.g., a plastic body) with a cross-sectional shape similar to an inward-facing asymmetrical C, and wherein the body is shaped to be placed proximal to a site (e.g., surgical site) and emit light onto the site from a plurality of directions while inhibiting the light from radiating away from the outside of the body.

19 Claims, 10 Drawing Sheets

(56) References Cited

U.S. PATENT DOCUMENTS

| | | |
|---|---|---|
| 7,874,982 B2 | 1/2011 | Selover |
| 7,909,761 B2 | 3/2011 | Banchieri et al. |
| 8,016,441 B2 * | 9/2011 | Birman et al. ............... 362/26 |
| 8,684,577 B2 * | 4/2014 | Vayser ...................... 362/573 |
| 8,740,780 B2 * | 6/2014 | Honda et al. ............... 600/177 |
| 2004/0184286 A1 * | 9/2004 | De Lamberterie ............ 362/559 |
| 2008/0064931 A1 | 3/2008 | Schena et al. |
| 2010/0249523 A1 | 9/2010 | Spiegal et al. |
| 2010/0315816 A1 * | 12/2010 | Madelin ...................... 362/294 |
| 2011/0021877 A1 | 1/2011 | Fortier et al. |
| 2012/0022333 A1 | 1/2012 | Main et al. |
| 2012/0116362 A1 | 5/2012 | Kieturakis |
| 2012/0130186 A1 | 5/2012 | Stopek et al. |

* cited by examiner

LIGHT GUIDE DIFFUSER, AND METHODS

CROSS-REFERENCE TO RELATED APPLICATION

This application claims the benefit of U.S. Provisional Application No. 61/578,428, filed Dec. 21, 2011, the contents of which are incorporated by reference in their entirety.

FIELD OF THE INVENTION

The present invention relates to devices and methods for illuminating surgical sites, implements and implants.

BACKGROUND

Providing good light to a surgical site can be problematic. Not only can overhead lights be unwieldy, they can be both a source of glare and of shadows simultaneously, making it difficult to see the surgical site and the video monitors. Head lamps also cast shadows, for example, of a surgeon's hands or instruments, and are intrinsically heavy (or require cumbersome connections to external light or power sources.)

Small lamps and other light-emitting structures are unnecessarily costly and complicated. They typically require bulbs, light-emitting diodes, or fiber-optical elements, as well as a source of power which potentially becomes an electric shock risk to the patient. Not only do they have multiple connections and bulky fixtures that complicate surgery, they can be problematic sources of heat. Also, a light fixture that incorporates elements such as light bulbs into a complex structure requires significant manufacturing costs.

Moreover, any light source—whether overhead or localized—can cause glares and reflections that are blinding or distracting. Light that glares off of monitors interferes with the ability of medical staff to monitor a patient's vital signs and light reflecting from steel or mirrored surfaces and instruments can interfere with a surgeon's focus.

SUMMARY

The invention relates to a surgical-site lighting device that connects to an existing light source and illuminates a surgical site from multiple directions without causing glares and reflections. The device is structured so that, when placed near a surgical site with portions of the device extending around opposite sides of the site, light from the source is reflected within the device and emitted onto the site. Moreover, the outer shell of the device provides a substantially opaque shield that prevents the light from causing glares and reflections in the surrounding environment. Since devices of the invention do not need to incorporate light bulbs, optical fibers, or electrical components, they can be manufactured inexpensively, for example, from molded plastic. Thus methods and devices are provided that can be used to provide good light to a surgical site, allowing a surgeon to perform surgery in good view without interference from shadows, structures, glares, heat, and other problems.

In certain embodiments, devices of the invention provide a shell with an open C-shaped cross-sectional profile with the open portion of the C facing inwards and downwards. The shell includes a substantially opaque material with an inner reflective surface. Light is received within the shell through an adaptor that couples to a fiber optic light line. The light is both passed through a small slit in the reflector and reflected within the device using a multi-faceted reflector, the inner reflective surface, or both and onto the surgical site while the over-hanging upper portion of the shell shades the surgeon's eyes and the surrounding environment.

In certain aspects, the invention provides a device for lighting a surgical site that includes a connection feature to connect to a light source and receive light into the device and a shell configured to at least partially surround a surgical incision and diffuse the light inwards and downwards. The connection feature may be a fiber optic cable adapter where light is received into the device. The site is illuminated substantially evenly from all sides while the shell shades items outside of and above the device from the light. The shell may have a cross-sectional shape describable as an inward-facing asymmetrical C-like shape. The shell may be shaped such that an upper surface of the shell overhangs a lower surface of the shell. A multi-faceted (e.g., at least two) reflector may be disposed within the device to reflect the light from the source through the device. In certain embodiments, the reflector has a shape like a truncated pyramid and presents four facets angled away from one another. A slit may be provided through the reflector to allow some light to pass directly to the surgical area.

The shell may have an overall shape that allows portions of it to be disposed on distal sides of a surgical site. For example, in various embodiments, looking down on the shell reveals it have a shape approximating a U, O, D, L, V, C, H, Y, or J or a square, diamond, oval, ellipse, rectangle, or other polygon. In certain embodiments, an overall shape of the shell is circular or substantially circular (e.g., oblong or irregular). The shape also allows a surgical instrument to be applied at various angles to the incision/surgical site.

In certain aspects, the invention provides a method for illuminating a site of a medical procedure. The method includes receiving light into a shell surrounding a site of a medical procedure and diffusing, by means of the shell, the light inwards and downwards towards the site substantially evenly from all sides while shading items outside of and above the device from the light. In some embodiments, diffusing the light comprises reflecting the light from a reflective surface disposed around a majority of an inside surface of the shell. Light can be received into the shell from any suitable source, such as a fiber optic cable, and reflected off of one or more internal reflectors.

In certain aspects, the invention provides a surgical site light having a plastic body with a cross-sectional shape similar to an inward-facing asymmetrical C, wherein the body is shaped to be placed proximal to a surgical site and emit light onto the site from a plurality of directions while inhibiting the light from radiating away from the outside of the plastic body. In some embodiments, the body is spaced away from the site in all directions when in use.

In some embodiments, the C-shaped plastic structure forms a circle on itself and is open in the middle. Devices of the invention can be made from plastic or other compatible matter. Materials can be used that are rigid, non-translucent, or both. The non-translucent nature of the device prevents light from reflecting in any direction that would interfere with visual acuity.

In certain embodiments, the upper surface a device is wider and overhangs the lower surface to prevent light from interfering with visual acuity and to focus the light in an inferior and center direction onto the procedure site. The inner surface may be covered with a reflective coating, and angled in a manner that further allows light to be focused in a central and inferior direction. Light enters the device via fiber optic cable, which can be connected to a variable output light source. In some embodiments, both the cable and the light source are separate from, and can be coupled to, and uncoupled from, the device. The fiber optic cable can be held in place by the cable adaptor. The adaptor may not only accommodate the cable but also be long enough to cover all metal parts of the cable thus eliminating any contact between any metal parts of the cable and patient.

In certain embodiments, once light enters the device it encounters the light reflector. The reflector is pyramidal in shape and covered with a reflective coating. This shape allows for reflectivity around the metalized inner surface of the device. The reflector can include a slit in the middle to allow some passage of light directly into the inner circle. The slit may be large enough to allow for light to pass through, and thereby eliminating shadows at the point of entry, but small enough to allow ample light to be reflected around the remainder of the device.

The device can be manufactured to different diameters to allow for different surgical applications. An adhesive strip can be applied to the device (e.g., during the manufacturing process) and the device incorporated into the surgical drape. The device can undergo gamma radiation sterilization as well as ethylene oxide sterilization and thus be used in sterile or non-sterile applications.

DETAILED DESCRIPTION

The present invention provides methods and devices for illuminating a surgical site. Devices and methods of the invention can be used with any surgical instrument in any surgical procedure that requires illumination. Examples of surgical procedures that may employ devices and methods of the invention include without limit laparoscopic and endoscopic procedures, insertion of anchors and fixation devices, including rods, plates and cables, trochars, injection ports or any procedure benefiting from good illumination.

Figure 1A:
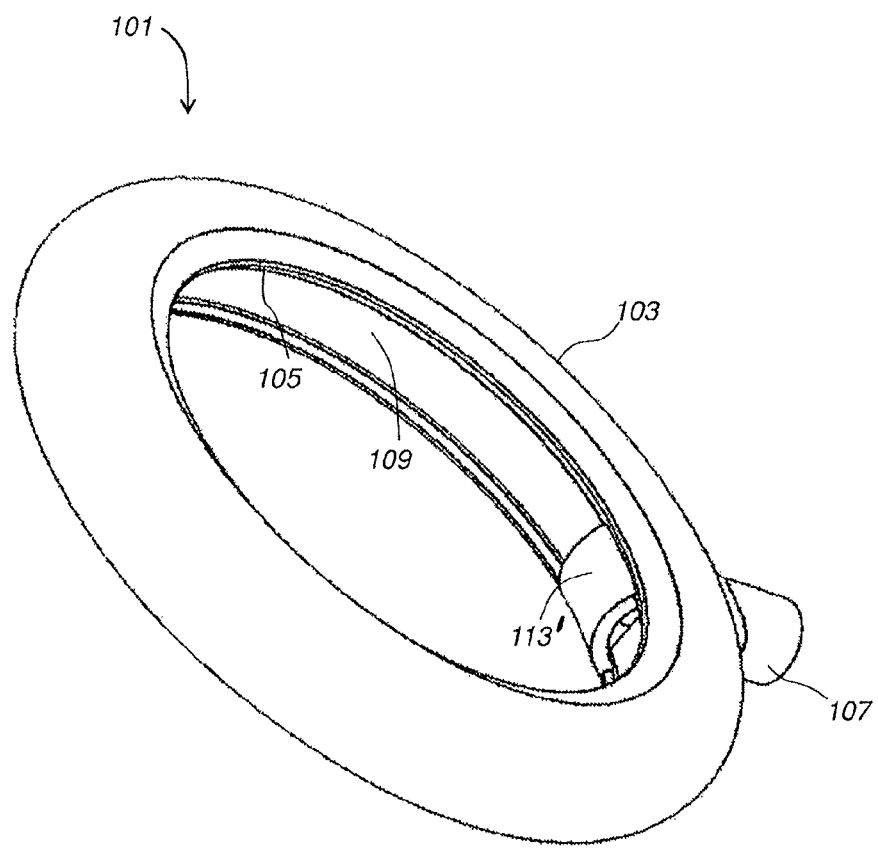
FIGS. 1A-1E show a device of the invention.

FIGS. 1A-1E show a device of the invention. FIG. 1A gives a perspective view of device 101 showing shell 103 and connection feature 107. Reflector 113'(or 113) can be seen mounted substantially within shell 103.

Figure 1B:
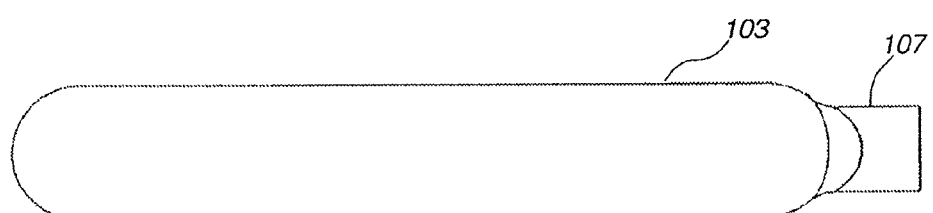
Figure 1C:
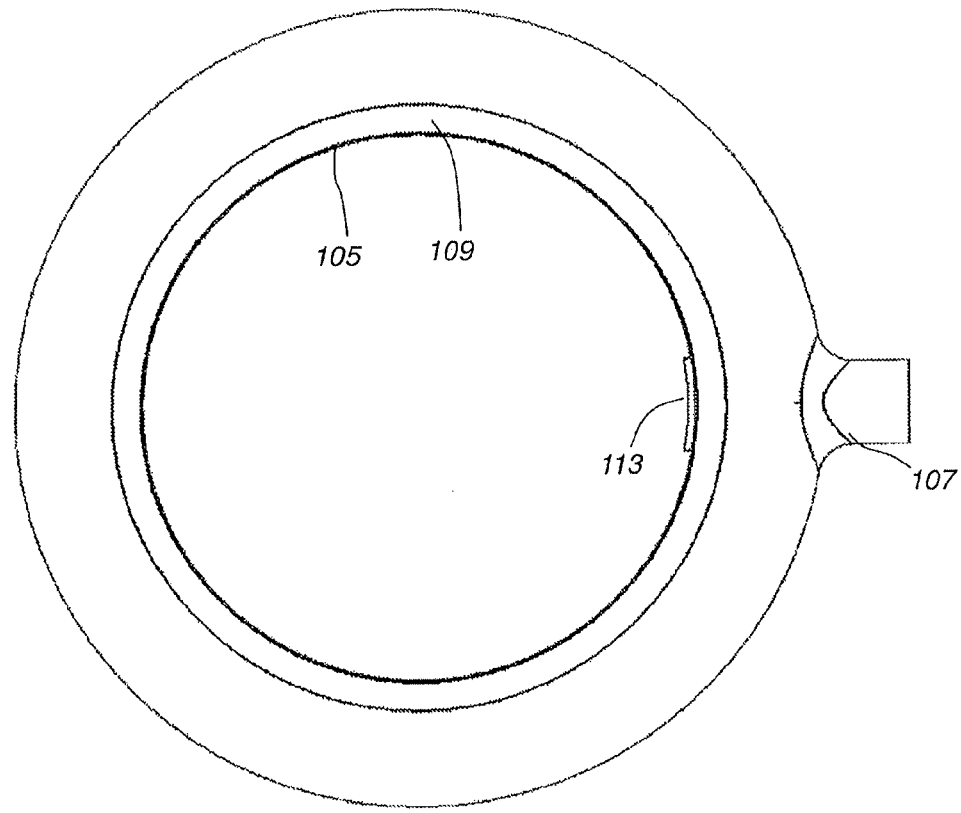

FIG. 1B gives a side view of device 101. FIG. 1C gives a bottom view, revealing a portion of reflector 113 and overhang 105 presenting surface 109 in a downward (inferior) direction.

Figure 1D:
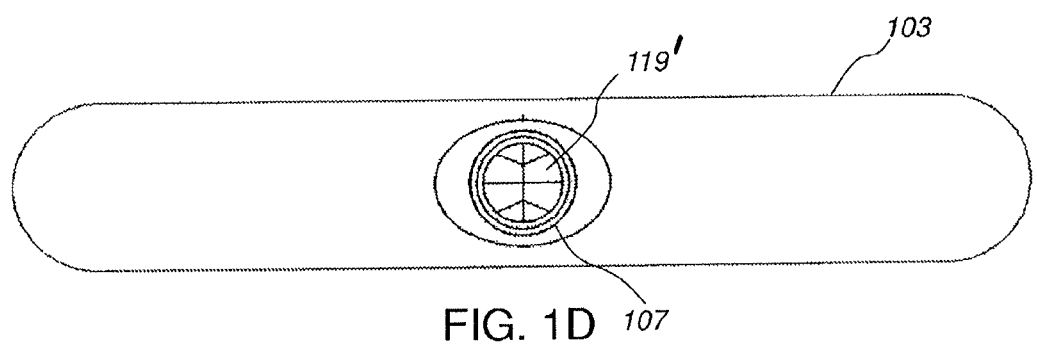
Figure 1E:
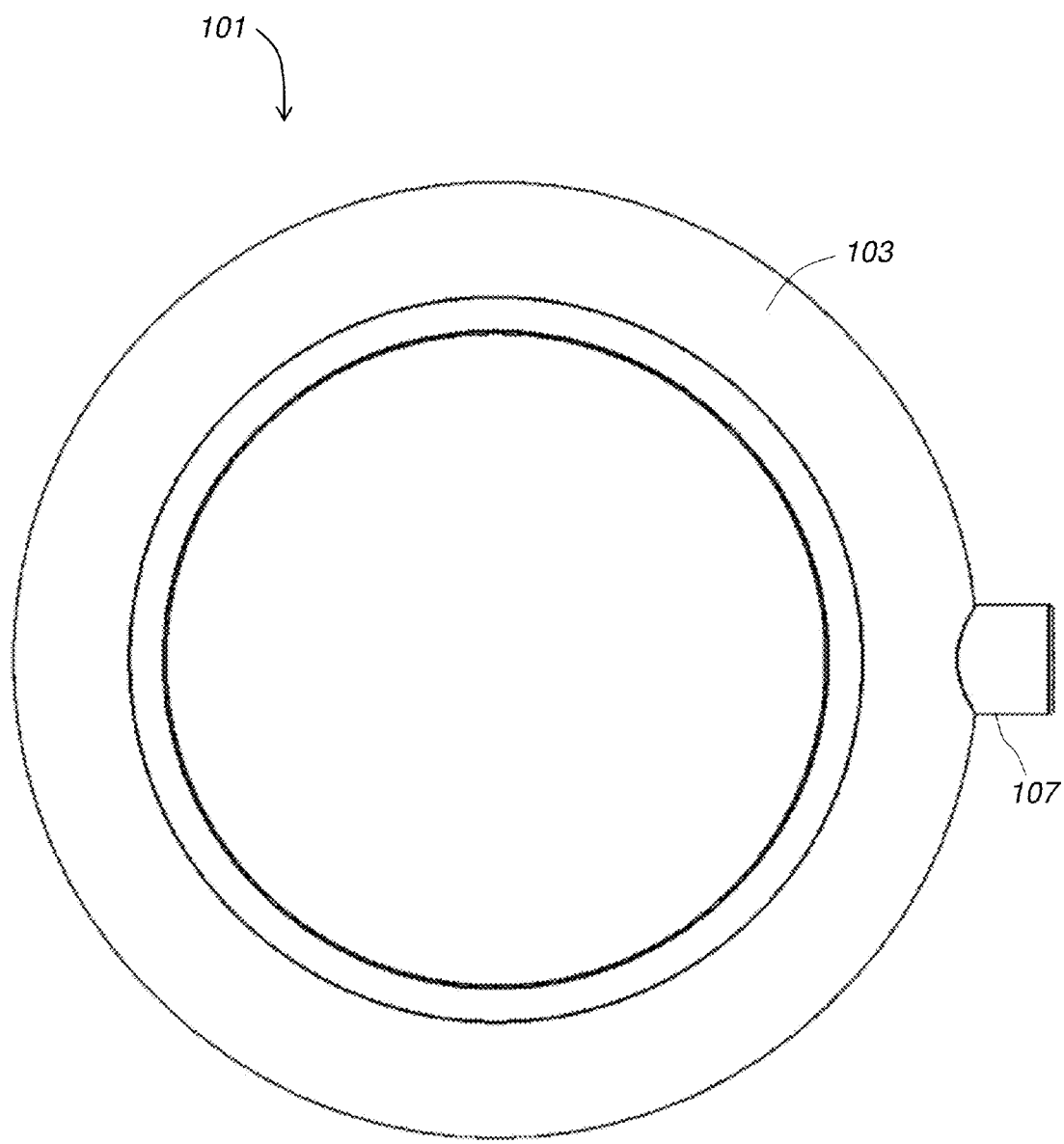

FIG. 1D shows a front view through connection feature 107, revealing faceted surface 119' of reflector 113'. FIG. 1E gives a top view of device 101.

FIGS. 2A-2D show reflector 113 according to certain embodiments. As can be seen, for example, in FIG. 2A, reflector 113 presents faceted surface (e.g., multi-faceted surface) 119 towards incoming light arriving through connection feature 107. Due to the fact that surface 119 presents a plurality of surfaces angled away from one another, incoming light is reflected in a plurality of direction into shell 103. Within shell 103, the light is reflected and re-reflected throughout the shell while also being reflected out of the shell in an inward and downward direction. While FIG. 1A, for example, shows shell 103 being substantially circular in overall shape, it will be appreciated that other shapes are possible and can also be adapted to reflect light inwardly and downwardly. For example, any closed curve or polygon may perform as described, as will shapes with a plurality of arms radiating away from reflector 113, such as a V shape or U shape with reflector 113 and connection feature 107 at a point such as the base of the U or V, alone one of the arms, or at one or both of the tips of the U or the V.

Figure 2A:
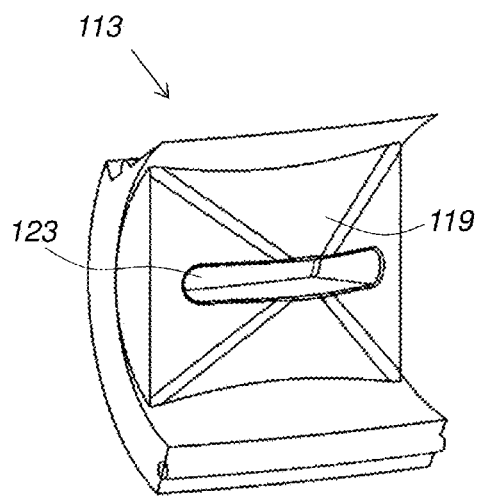
FIGS. 2A-2D show a multi-faceted reflector according to certain embodiments.
Figure 2B:
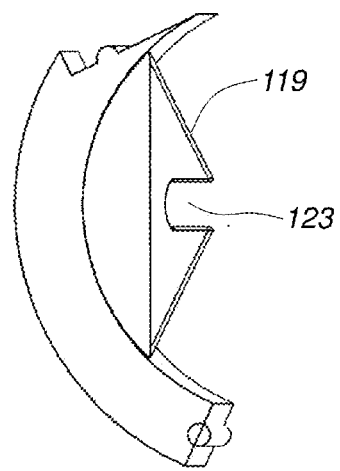

FIG. 2B shows structural features that can be included at the top and bottom of reflector 113 allowing it to be snapped into place, or fitted into, shell 103.

Figure 2C:
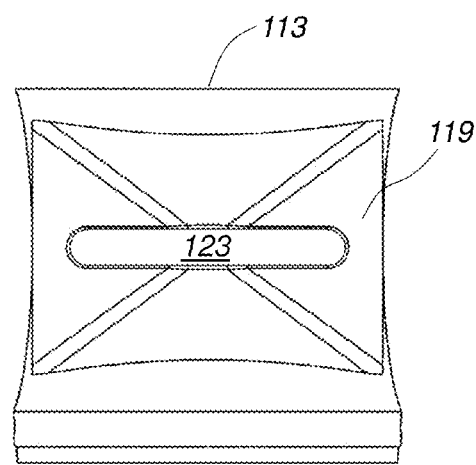

FIG. 2C illustrates that slit 123 extends completely through reflector 113. Slit 123 can be provided to allow light to pass directly from the light source to the surgical sight. The aperture area of slit 123 can be varied by design (e.g., from zero to a few $cm^2$) to modulate a ratio of an amount of light penetrating directly through slit 123 to the site to an amount of light reflected via internal surface 109 of shell 103 to the site. Different surgeons or different applications may benefit from one ratio or another according to preferences or circumstances.

Figure 2D:
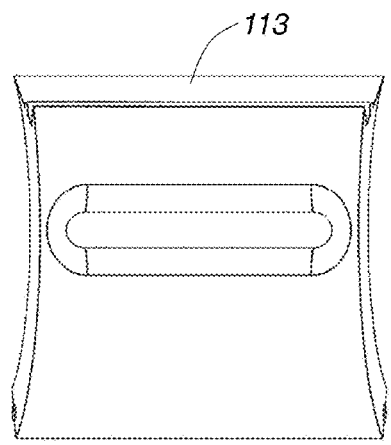

FIG. 2D shows the aperture in the back of the housing of reflector 113 for slit 123.

Figure 3:
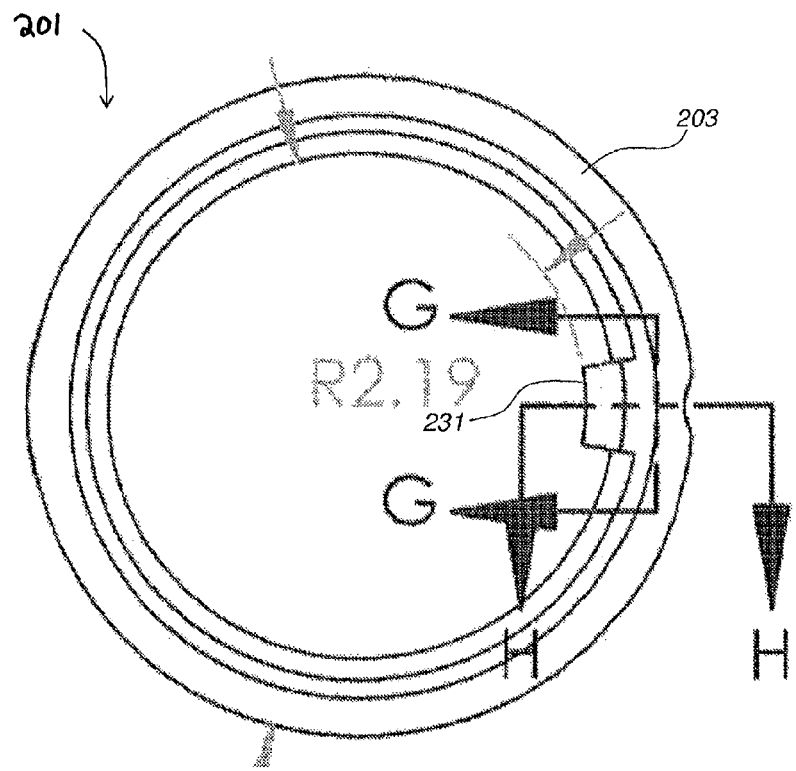
FIG. 3 shows a device according to certain embodiments.

FIG. 3 shows a device 201 according to alternative embodiments. Device 201 as shown in FIGS. 3-6 is constructed from an upper shell 203 and a base shell 204.

Figure 4:
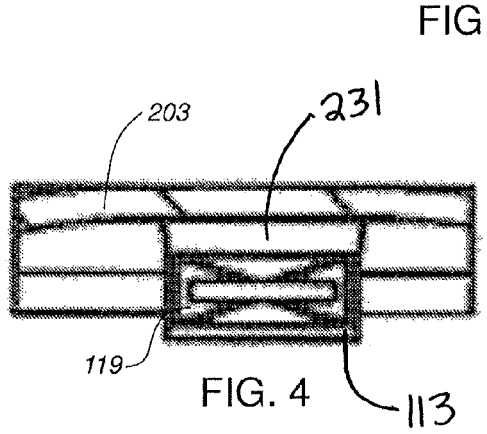
FIG. 4 shows a section of the device shown in FIG. 3.

FIG. 4 shows a section of device 201 taken along line G shown in FIG. 3. As can be seen in FIG. 4, boss 231 holds reflector 113 in place (e.g., according to geometry shown in FIGS. 9 and 10) so that facets 119 are exposed through coupling 107.

Figure 5:
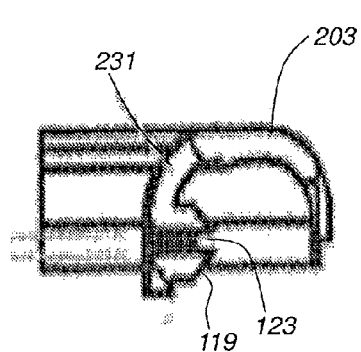
FIG. 5 shows a section of the device shown in FIG. 3.

FIG. 5 shows a section of device 201 along line H shown in FIG. 3. As illustrated here, the arrangement of boss 231 and reflector 113 positions slit 123 to allow light to pass through and illuminate a surgical site.

Figure 6A:
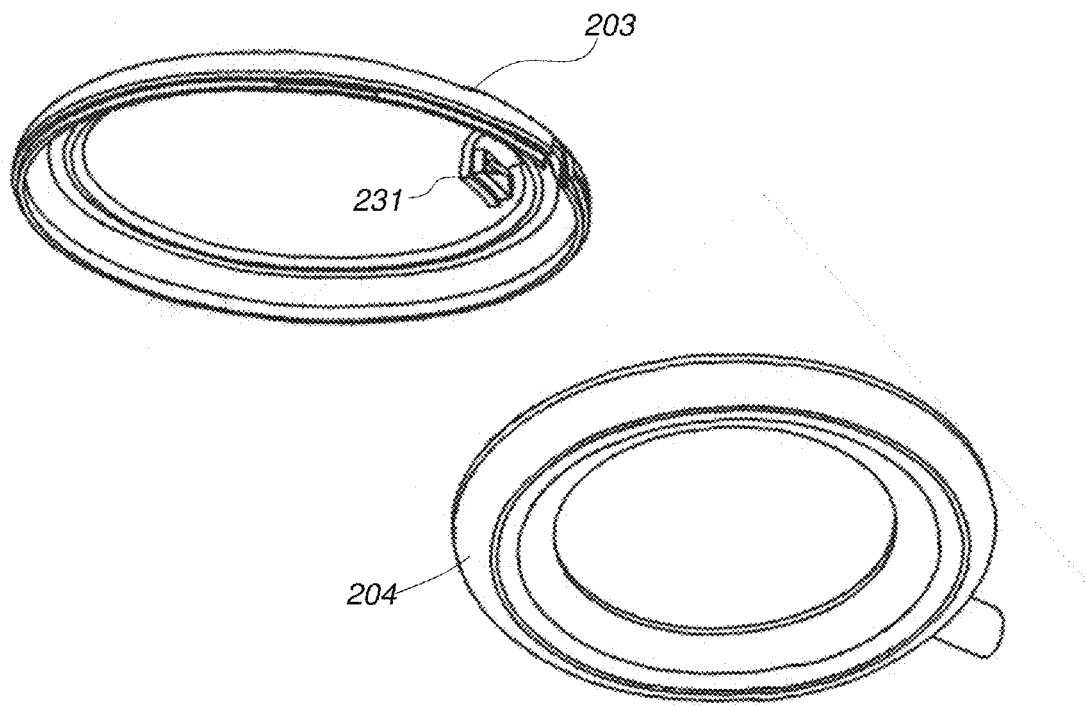
FIGS. 6A and 6B show components of a device according to certain embodiments.

FIGS. 6A gives a perspective view of upper shell 203 and a base shell 204 of device 201 according to certain embodiments. Not only does manufacturing device 201 according to a two-component design provide an easy to mold and lightweight snap-together assembly, by positioning connection feature 107 and boss 231 on opposed components, the arrangement for assembling the shapes is made visually evident. This allows a user-assembled device to be provided, for example, as two separate components. In some embodiments, upper shell 203 and base shell 204 are packaged and shipped one nested within the other, or as stacks of each separately nested, for compact packaging and shipping.

Figure 6B:
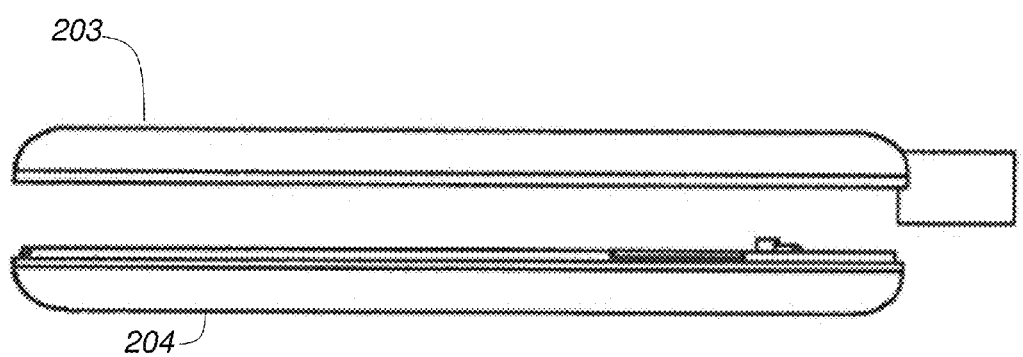

FIG. 6B illustrates assembly of upper shell 203 and base shell 204. Upper shell 203 and a base shell 204 can each be fabricated separately, of a suitable material (e.g., plastic). An inside surface of upper shell 203, base shell 204, or both can be coated with a reflective material. Components of devices of the invention can be formed of any suitable surgical material such as for example, plastic, surgical stainless steel, resin, glass, foil, fiberboard, other materials known in the art, or combinations thereof. Further suitable materials may include epoxy, titanium or other metals, ceramics, composites, rubbers, or polymers.

Reflective surface 109 on the inside of shell 103 can be provided by any suitable means. In some embodiments, reflective surface 109 includes a coating of a reflective material, such as a metallic material. In some embodiments, surface 109 includes foil disposed within shell 103. Surface 109 may include a mirror, for example, a glass, crystal, or plastic minor, that is curved and disposed within shell 103.

Figure 7:
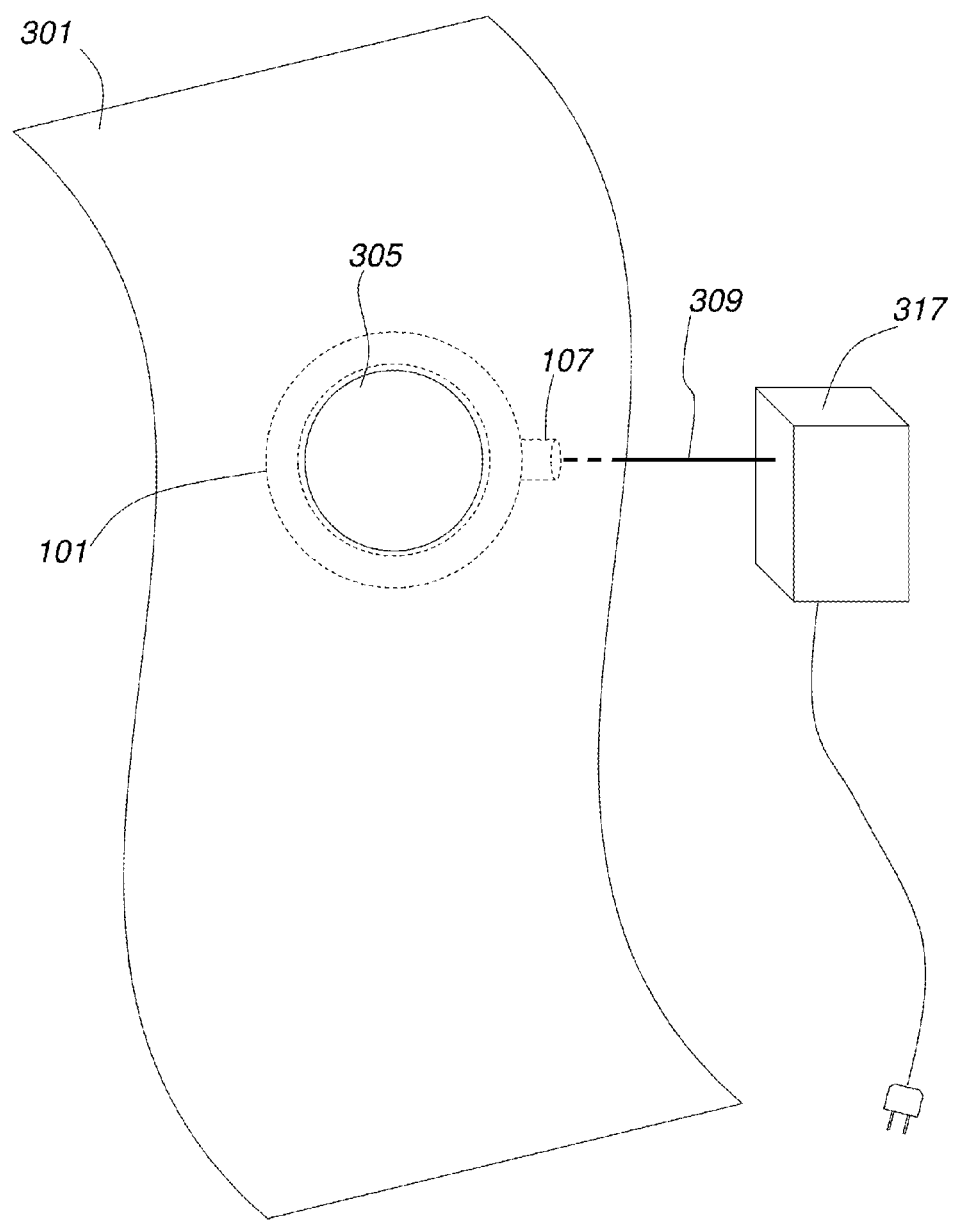
FIG. 7 illustrates use of the device according to certain embodiments.

FIG. 7 illustrates use of the device according to certain embodiments. Sterile surgical sheet 301 may be placed over a site for an incision. Sheet 301 may have hole 305 for surgery. Device 101 may be located under sheet 301 and connected to light source 317 via fiber optic cable 309.

Device 101 includes connection feature 107 which can include an adaptor to couple to fiber optic cable (e.g., fiber optic light line) 309 from light source 317. The light source may include glass fiber optic cables, plastic fiber optic cables or any other suitable means for transmitting and emitting light. Light source 317 may be any suitable device for producing light such as, for example, a halogen or incandescent light box or other light source readily available in most hospital settings. Suitable light sources are available from Welch Allyn Inc. (Skaneateles Falls, N.Y.) The light source may have any suitable power level.

In certain embodiment, light source 317 is a the XLS-300 High-Powered 300 W xenon light source from Olympus Corporation (Shinjuku, Tokyo, JP). Any other suitable light source capable of producing light that is transmitted via the light transmitters, such as fiber optic cables, may also be used. Light sources and optic cables are discussed in U.S. Pat. Nos. 5,850,496 and 5,115,126 and surgical illumination generally is discussed in U.S. Pat. Nos. 5,785,648; 6,616,603; 7,150,714; and 5,353,786, the contents of each of which are incorporated by reference.

Providing device 101 with circular or other open-format morphology of shell 103 allows a surgeon to work freely in the area surrounded by device 101. In some embodiments, an outer diameter of device 101 between about 2 inches and about 10 inches. In certain embodiments, an outer diameter of device 101 is between 4 and 8 inches, or about 5 to about 7 inches. Moreover, device 101 is spaced away from the incision or any surgical instruments. Surgical light is discussed in U.S. Pat. Nos. 7,909,761; 5,488,696; and 4,605,990, the contents of each of which are incorporated by reference in their entirety.

In some embodiments, device 101 is provided with an adhesive, such as a peel-and-stick adhesive on one surface. Removing the peel-off backing allows sheet 301 to be fixed into place on device 101. In certain embodiments, a device 101 is provided with a sheet 301 attached, for example, with an adhesive.

While reflector 113 is discussed herein having a pyramidal aspect, other embodiments are within the scope of the invention. In some embodiments, reflector 113 has two facets. Facets of reflector 113 may be flat, curved, or irregular.

Figure 8A:
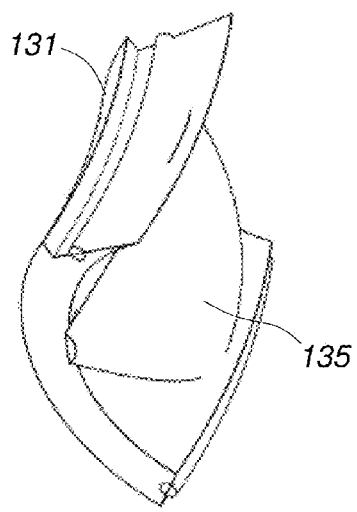
FIG. 8A-8D show a reflector according to certain embodiments.
Figure 8B:
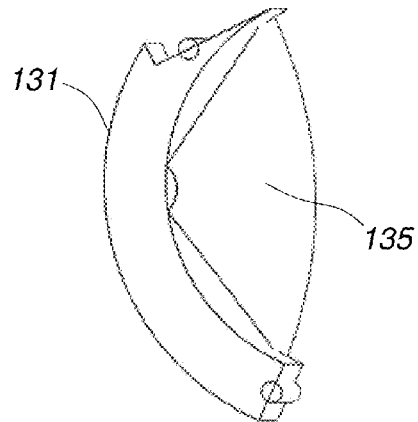
Figure 8C:
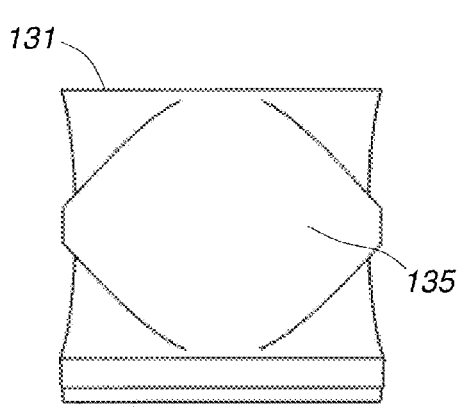

FIG. 8A gives a perspective view of a reflector 131 according to certain embodiments. As can be seen, for example, in side view in FIG. 8B or front view in FIG. 8C, reflector 131 may have a substantially convex curved face 135 and operate to provide the benefits of the invention.

Figure 8D:
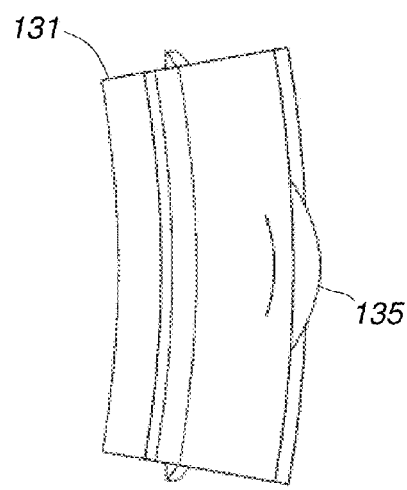

FIG. 8D shows a top view of reflector 131, illustrating the outer housing—which may be Plastic—and face 135. This assemblage can be assembled into device 101. Preferably, reflector 113, reflector 131, or the like is assembled into device 101 opposed to connection feature 107 according to a geometry that reflects light throughout the device.

Figure 9A:
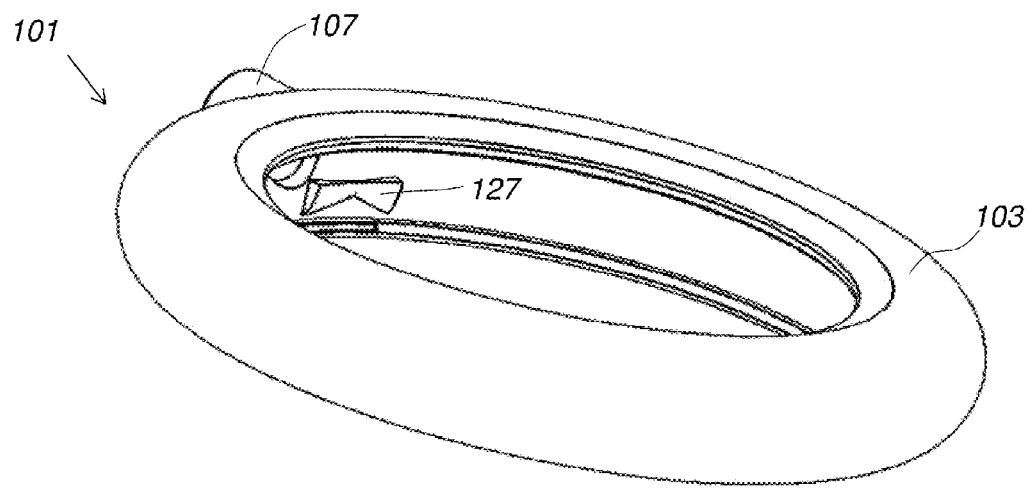
FIG. 9A-9B illustrate an of arrangement of components in a device of the invention.
Figure 9B:
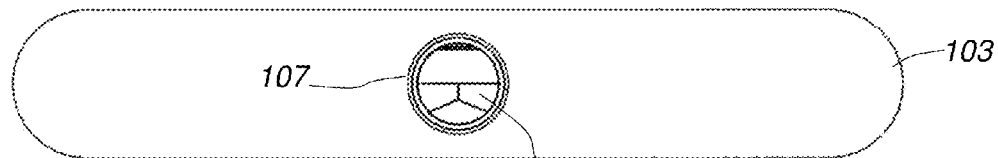

FIG. 9A-9B illustrate a geometry of arrangement of components within device 101. Reflector 127, which may have the illustrated morphology or any other morphology described herein or useful for illumination, is opposed to connection feature 107.

Figure 10A:
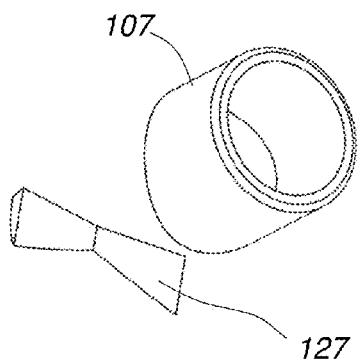
FIG. 10A-10B gives a detailed view of an arrangement of components.
Figure 10B:
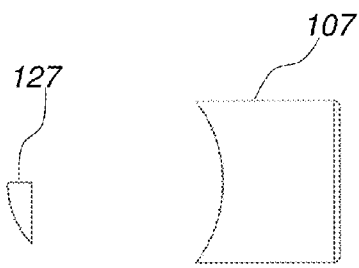

FIG. 10A-10B show a spatial relationship between reflector 127 and connection feature 107. In some embodiments, connection feature 107 has a substantially cylindrical portion defining an axis. The axis of feature 107 may extend into a surface of the reflector. However, in certain embodiments, for example where slit 123 is present, the axis of feature 107 does not intersect the reflector at all but, rather, pass by or through it (e.g., through slit 123).

Devices and methods of the invention provide significant advantages over prior systems for providing illumination during a surgical procedure. The device minimizes the requirement of cumbersome cables, headlights, overhead fixtures, and power sources, while allowing direction of light to an ideal location. Device 101 does not compromise or reduce the working area, as it is spaced away from the incision, and provides superior illumination of the procedure site without inducing glare or affecting the surgeon's visual acuity Devices and methods of the invention help people see a surgical field when overhead operating room lights need to be dimmed or turned off. The surgical site is illuminated without creating a glare on the monitor screen or in a person's eyes, creating a more efficient and safer environment for surgeons, operating room staff and patients.

Devices and methods of the invention improve efficiency or flow of surgical procedures by avoiding the need to repeatedly adjust overhead lights and thereby eliminate the need for the people's eyes to accommodate to different lighting conditions; increase the visibility of ports while changing instruments; eliminate the questionable practice of removing camera or light from inside patient's abdomen or pelvis to illuminate a surgical site; enhance visualization of the surgical field when preparing and inserting mesh and other implants; improve visualization of sharps on the surgical field reducing the risk of accidental punctures to staff; reduce the risk of injury to surgical assistants and OR staff by improving ability to monitor robotic arm movement during surgery; allow for estimation of blood loss around surgical ports; allow staff to maintain correct count of surgical instruments, sponges and sharps on the field as well as employed as a teaching device allowing students to see location of such ports/trochars/devices without turning on overhead lights.

Figure 11:
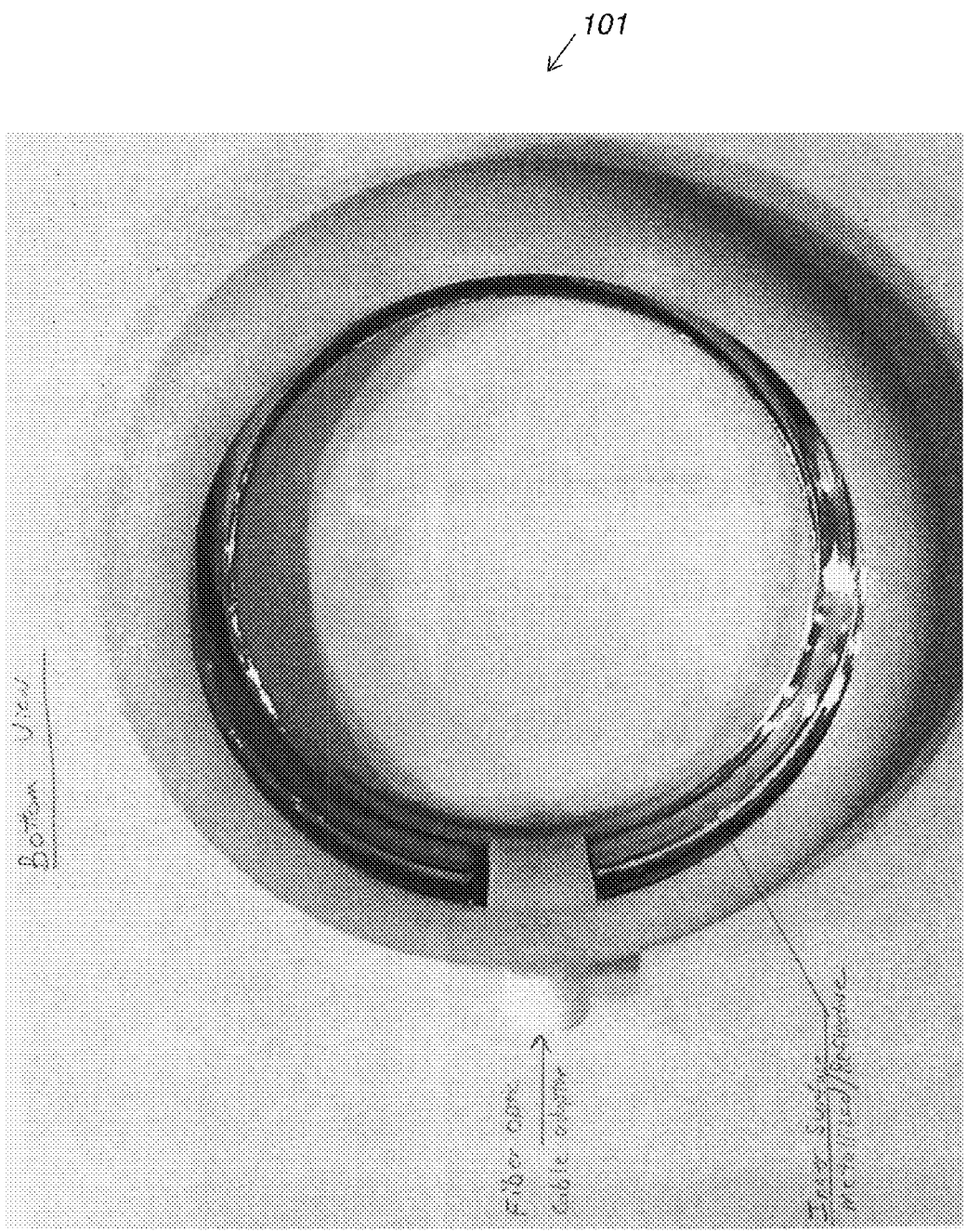
FIG. 11 is a reproduction of a photo of a device that was made.

FIG. 11 is a reproduction of a photo of a device that was made. Devices and methods of the invention are inexpensive to manufacture, and work in conjunction with existing operating room equipment and technology. Additional applications include invasive radiology, various imaging modalities and enhancing teaching techniques.

In certain alternative embodiments, devices and methods of the invention incorporate multiple structures to provide light both above and below the incision site. Dual-device structures are provided, for example, for use with single incision laparoscopic surgery procedures (SILS). Such procedures may employ an SILS port. See, e.g., U.S. Pub. 2012/0130186; U.S. Pub. 2012/0022333; U.S. Pub. 2011/0021877; and U.S. Pub. 2010/0249523, the contents of each of which are incorporated by reference in their entirety.

Two of device 101 that are permanently attached one on top of the other form multi-structure device of according to one alternative embodiment. The light port lies at the junction of the two light rings and is anchored in place during the manufacturing process to the upper lip of the lower ring. This forms a seal that prevents the escape of gasses from the body cavity during the laparoscopic procedure. The shell 103 of each device 101 is constructed from non-translucent material (e.g., plastic) and has a reflective inner surface 109.

In certain embodiments, the upper one of device 101 has two light adaptors. The first adaptor is in a longitudinal plane as above. The second light adaptor is oriented in a vertical plane and is used to provide light to the lower light ring. A direct connection between upper and lower devices 101 is aligned and forms a channel to allow light from the second adaptor to pass through the upper device 101 to the lower device 101. The light then encounters the light reflector, which will reflect light around the lower light device 101. Light is then directed by the reflective surface in an inferior direction thereby illuminating the body cavity and the in vivo surgical site. An inflatable seal located on the outer diameter of the upper device 101 may be provided to prevent gasses from escaping the body cavity. Single-incision procedures are discussed in U.S. Pub. 2012/0116362 and U.S. Pub. 2008/0064931, the contents of which are incorporated by reference.

Devices of the invention can be sterilized by means known in the art.

As used herein, the word "or" means "and or or", sometimes seen or referred to as "and/or", unless indicated otherwise.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A lighting device comprising:
   a shell having an asymmetrical C-shaped cross-sectional profile, the shell having an upper portion and a lower portion with the upper portion extending over the lower portion and extending further inwards than the lower portion to define the asymmetrical C-shaped cross-sectional profile of the shell, the C-shaped cross-sectional profile being asymmetrical about a plane including the boundary between the upper and lower portions; and
   a reflector mounted to the shell, the reflector positioned so that light from a light source is reflected by the reflector in a plurality of directions into the shell;
   wherein the asymmetrical C-shaped shell is configured to at least partially surround a pre-determined location and diffuse the light inwards and downwards, via the asymmetrical C-shaped shell, toward the pre-determined location substantially evenly from all sides while the upper portion of the shell shades items outside of and above the shell from the light.

2. The device of claim 1, wherein the reflector is directly mounted to the upper and lower portions of the shell.

3. The device of claim 1, wherein an overall shape of the shell is substantially circular.

4. The device of claim 1 wherein the cross-sectional profile of the shell comprises an inward-facing asymmetrical C-like shape.

5. The device of claim 4, wherein an inner surface of the shell comprises a reflective material.

6. The device of claim 1, wherein the reflector comprises four facets angled away from one another.

7. The device of claim 6, wherein the reflector comprises a slit extending through the reflector.

8. The device of claim 1, further comprising a connection feature mounted to the shell, the connection feature to connect to the light source and receive light into the shell.

9. The device of claim 8, wherein the connection feature comprises a fiber optic cable adaptor.

10. A method for illuminating a site, the method comprising:
    providing a shell having an asymmetrical C-shaped cross-sectional profile, the shell having an upper portion and a lower portion with the upper portion extending over the lower portion and extending further inwards than the lower portion to define the asymmetrical C-shaped cross-sectional profile of the shell, the C-shaped cross-sectional profile being asymmetrical about a plane including the boundary between the upper and lower portions;
    mounting a reflector to the shell;
    positioning the shell to at least partially surround a pre-determined location; and
    providing light from a light source to the reflector so that the light is: (i) reflected by the reflector in a plurality of directions into the shell, and (ii) diffused inwards and downwards, via the asymmetrical C-shaped shell, toward the pre-determined location substantially evenly from all sides while the upper portion of the shell shades items outside of and above the shell from the light.

11. The method of claim 10, wherein the shell has an overall shape that is substantially circular; and
    wherein the cross-sectional profile of the shell is an inward-facing asymmetrical C-like shape.

12. The method of claim 10, further comprising providing the light into the shell from a fiber optic cable.

13. The method of claim 10, wherein the reflector includes two or more facets angled away from one another; and
    wherein the reflector reflects the light in the plurality of directions into the shell via the two or more facets.

14. The method of claim 13, wherein the reflector comprises an aperture configured to allow some of the received light to pass through the reflector without interacting with the facets.

15. The method of claim 10, wherein the shell comprises a connection feature at which the light is received and the reflector is disposed proximal to the connection feature and substantially within the shell.

16. The method of claim 15, wherein the connection feature comprises an adaptor configured to fasten to the light source that provides the light.

17. The method of claim 15, wherein diffusing the light comprises reflecting the light from a reflective surface disposed around a majority of an inside surface of the shell.

18. The method of claim 17, wherein the reflective surface comprises a plastic material; and
    wherein the reflector is mounted to the upper and lower portions of the shell.

19. A lighting device comprising:
- a shell with an inward-facing asymmetrical C-shaped cross-sectional profile, the shell having an upper portion and a lower portion with the upper portion extending over the lower portion and extending further inwards than the lower portion to define the inward-facing asymmetrical C-shaped cross-sectional profile of the shell, the C-shaped cross-sectional profile being asymmetrical about a plane including the boundary between the upper and lower portions;
- a connection feature mounted to the shell, the connection feature to connect to a light source and receive light into the shell;
- a reflector mounted to the upper and lower portions of the shell, the reflector positioned so that light from the light source is reflected by the reflector in a plurality of directions into the shell;
- wherein the inward-facing asymmetrical C-shaped shell is configured to at least partially surround a pre-determined location and diffuse the light inwards and downwards, via the inward-facing asymmetrical C-shaped shell, toward the pre-determined location substantially evenly from all sides while the upper portion of the shell shades items outside of and above the shell from the light;
- wherein an overall shape of the shell is substantially circular;
- wherein an inner surface of the shell includes a reflective material disposed around a portion of the inner surface of the shell, the reflective material configured to diffuse the light toward the pre-determined location;
- wherein the reflector is disposed proximal to the connection feature and substantially within the shell;
- wherein the reflector includes two or more facets angled away from one another, and the reflector reflects the light in the plurality of directions into the shell via the two or more facets;
- wherein the reflector includes an aperture therethrough configured to allow some of the received light to pass through the reflector without interacting with the facets; and
- wherein the pre-determined location is a site of a medical procedure.

* * * * *